(12) United States Patent
Laustsen et al.

(10) Patent No.: US 6,316,240 B1
(45) Date of Patent: Nov. 13, 2001

(54) RECOVERY OF A GLYCOSIDASE OR PEPTIDASE FROM A CULTURE BROTH AT HIGH PH

(75) Inventors: Mads Aage Laustsen, Lyngby (DK); Curran Matthew Simpson, Youngsville, NC (US); Michael John O'Reilly, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/489,712

(22) Filed: Jan. 24, 2000

Related U.S. Application Data
(60) Provisional application No. 60/118,757, filed on Feb. 5, 1999.

(30) Foreign Application Priority Data

Jan. 25, 1999 (DK) .............................................. 1999 00085
Oct. 18, 1999 (DK) .............................................. 1999 01491

(51) Int. Cl.$^7$ ............................... C12N 9/48; C12N 9/50; C12N 9/24; C12N 9/26
(52) U.S. Cl. .......................... 435/212; 435/200; 435/201; 435/219
(58) Field of Search ..................................... 435/212, 219, 435/223, 224, 225, 200, 201, 203, 205, 207, 208, 209, 210, 211

(56) References Cited

U.S. PATENT DOCUMENTS
5,340,926 * 8/1994 Lowe et al. ........................ 530/423

FOREIGN PATENT DOCUMENTS
| | | |
|---|---|---|
| 0 122 080 | 10/1984 | (EP) . |
| 0 173 215 | 3/1986 | (EP) . |
| 0 331 464 | 9/1989 | (EP) . |
| 0 373 325 | 6/1990 | (EP) . |
| 574050A1 | 12/1993 | (EP) . |
| WO 83/04418 | 12/1983 | (WO) . |
| WO 97/23604 | 7/1997 | (WO) . |

OTHER PUBLICATIONS

Grohmann et al., "Flocculation chemicals: inorganic substances", DVGW–Schriftenr., Wasser 42: 43–58 (1985).*

Collingwood et al., "An M(III)–facilitated flocculation technique for enzyme recovery and concentration", J. Biochemical Biophys. Methods 17 : 303–310 (1988).*

* cited by examiner

*Primary Examiner*—Sandra E. Saucier
(74) *Attorney, Agent, or Firm*—Elias J. Lambiris; Jason I. Garbell

(57) ABSTRACT

The present invention relates to a method for recovering a glycosidase or a peptidase from a culture solution from an unsolubilized state within said solution to a solubilized state within said solution.

11 Claims, No Drawings

RECOVERY OF A GLYCOSIDASE OR PEPTIDASE FROM A CULTURE BROTH AT HIGH PH

CROSS-REFERENCE TO RELATED APPLICATIONS

This application claims the benefit of U.S. Provisional application No. 60/118,757, filed Feb. 5, 1999, the contents of which are fully incorporated herein by reference.

FIELD OF INVENTION

The present invention relates to a method for recovering a glycosidase or a peptidase from a culture broth, from an insoluble state within said broth to a soluble state within said broth.

BACKGROUND ART

Recovery of a protein of interest from a culture broth may be hampered by the fact that a significant amount of the protein of interest is not in a solubilized form.

Said problem may occur when e.g. the protein of interest is bound to components in the sludge as such or due to the fact that a significant amount of the protein of interest is precipitated or crystallized prior to harvest from the culture-broth.

Sludge binding of a protein of interest denotes that the protein is bound to solids in the culture medium, such as cell solids or other solid components in the medium.

In relation to an effective recovery of the protein this may be a significant problem.

A number of methods have been applied for solving or minimizing said problem.

In many cases low or varying recovery yields have been accepted, in other cases the problem has been diminished through additions of e.g. ionic/nonionic surfactants, salts, anti/defoaming agents, alcohols, substrate or substrate analogs for the enzyme in question.

In many cases such techniques have been of low efficiency, in other cases complicated procedures have been developed (e.g. liquid-liquid separation systems) requiring large amounts of agent(s) added.

Some examples are found in the recovery of lipases, which are enzymes with a high tendency towards binding to fermentation solids and/or potential filter aids used in recovery.

WO 97/23604 describes a method for recovering of a lipase from a fermentation broth.

Essential steps in the described method comprise the use of both a nonionic surfactant and an alcohol so that a final composition is obtained which contains the microbial protein (preferably a lipase), the nonionic surfactant and the alcohol. See e.g. claim 1 of said WO 97/23604 document.

EP 0574050A1 describes a method for recovering of a hydrophobic product, preferably a lipolytic enzyme, (see column 3, line 47–50) from a fermentation broth. Essential steps in the described method comprise the use of both a nonionic surfactant and a salt in the process. See e.g. claim 1.

*Journal of Biotechnology*, 26 (1992) 111–142 is a review article describing the state of the art for different purification strategies of a lipase. On page 129 it is mentioned that lipase purification is generally hampered by the problem of solubilization of the lipase. The article summarizes the state of the art solutions to this problem which comprise very complex purification strategies, such as Liquid-liquid extraction, aqueous two-phase systems, specific membrane processes, and immunopurification.

For proteins precipitated or crystallized prior to harvest of broth, no real efficient methods exist today. Examples of solubilizing with large amounts of solubilization agents are typically tried (e.g. urea). Other examples are solid-solid separation techniques wherein the precipitated or crystallized protein in question is separated from the other solids in the broth,—such separations are often not possible and are always complicated.

SUMMARY OF THE INVENTION

The problem to be solved by the present invention is to provide a simple and effective method for recovering a protein of interest, preferably a glycosidase or a peptidase, from a culture broth, wherein a significant amount of the protein of interest is NOT in a soluble form within said culture broth.

The invention is based on the present inventors having identified that a protein of interest in a culture broth, particularly a glycosidase or peptidase, wherein a significant amount of the protein is NOT in a soluble form at pH 7.5 within said culture broth, can very efficiently be recovered by the use of extreme pH values, i.e. pH values from pH 9.5 to pH 13.

Accordingly, the invention relates to a method for recovering a protein of interest, preferably a glycosidase or a peptidase, from a culture broth comprising a cell capable of producing the protein, wherein less than 80% of the protein of interest is in a soluble form at pH 7.5 within said culture solution, comprising:

adjusting the pH of the culture broth to a pH value from pH 9.5 to pH 13; and b) removing the cells from the broth to obtain a solution comprising the protein of interest.

The term "a culture broth" denotes herein a culture medium comprising a protein of interest and a cell capable of producing the protein of interest. Said culture broth may comprise any further components, in particular components generally used for fermentation of a cell.

The term "wherein less than 80% of the protein of interest, at pH 7.5, is in a soluble form within said culture broth" is a term directed to the general problem to be solved herein, i.e. to recover a protein of interest wherein a significant amount of the protein of interest is not in solution.

Whether or not a "culture broth" complies with this criterion is herein defined by the fact that the concentration of the protein of interest in the supernatant of the culture solution has a concentration of less than 80% of the total concentration of the protein of interest in the culture solution as such. A supernatant is the aqueous medium obtained by, e.g., centrifugation under conditions sufficient to remove the cells, i.e., obtain a cell-containing pellet.

The term concentration denotes amount of protein (dry matter) per liter (e.g. g/l) or protein activity per liter.

The term "at pH 7.5" denotes herein that the supernatant is separated (preferably by centrifugation) from the culture solution as such at pH 7.5.

The concentration of the protein of interest in, respectively, the supernatant and the culture broth as such may then afterwards be measured at this pH 7.5 or at a different pH.

This will depend on the specific protein of interest and the specific culture broth and it is within the skilled persons general knowledge to decide this (see below for a further discussion of this).

Alternatively this may be expressed as:

A "culture solution" complies with the criteria set herein if:

$\text{Prot.}_{conc.\ sup.}/\text{Prot.}_{conc.\ Cul} \times 100 < 80$; at pH 7.5; wherein $\text{Prot.}_{conc.\ sup.}$ is the concentration of the protein of interest in the supernatant of the culture broth;

$\text{Prot.}_{conc.\ Cul}$ is the total concentration of the protein of interest in the culture broth as such.

Preferably, said concentration of the protein of interest in the supernatant is less than 70%; more preferably less than 55%, even more preferably less than 40% and most preferably less than 25% of the concentration of the protein in the whole culture.

The actual methods for measuring the concentration of the protein of interest are done according to standard methods known in the art and adjusted to the specific protein of interest.

When the concentration of the enzyme is measured in the culture broth as such, the methods to be used shall of course be methods that solubilize the insoluble fraction of the protein of interest before the actual measurement of the concentration of the protein of interest within said culture broth.

Numerous such methods are known in the art such as methods refined for hydrophobic or precipitated proteins, comprising methods using high dilution, addition of detergents, urea etc.

It is within the general knowledge of the skilled person to choose the specific methods according to the criteria outlined above.

It should in this connection here be noted that none of the culture solutions disclosed in WO 97/20921 fulfill these criteria, since the problem of said disclosure had nothing to do with the problem of recovering proteins that were not in solution.

Accordingly, all of the specific culture solutions disclosed in the WO 97/20921 document were culture solutions wherein the protein of interest in the supernatant of the culture solutions had a concentration of more than 80% of the total concentration of the protein of interest in the culture solution as such.

An advantage of the method, as described herein, is that the adjustment of the pH from pH 9.5 to pH 13 directly mediates solubilization of the protein of interest.

Accordingly, the solids (e.g. cells) may be separated from the protein of interest by simply spinning down the solids and recovering the supernatant. The method described herein allows this to be performed without the addition of compounds such as ionic/nonionic surfactants, salts, anti/defoaming agents, and specially alcohols, as were described as essential steps in the prior art methods discussed in WO 97/23604; and in EP 0574050A1.

Further, the method provides very high final yields of the protein of interest as illustrated by Example 1 of the present invention.

Embodiment(s) of the present invention is (are) described below.

DETAILED DESCRIPTION OF THE INVENTION

A culture broth comprising a cell capable of producing a glycosidase or a peptidase, wherein more than 20% of the protein of interest, at pH 7.5, is NOT in a soluble form within said culture broth:

As described in the background section above, a protein of interest may not be in a soluble form within a culture solution due to, e.g., that the protein of interest is bound to components in the sludge as such and/or due to a significant amount of the protein of interest being precipitated or crystallized prior to harvest from the culture broth.

Sludge binding of a protein of interest denotes that the protein is bound to solids in the culture such as cell solids or other solid components in the broth.

Accordingly, in preferred embodiments the invention relates to:

a method, wherein more than 20% of the protein of interest, at pH 7.5, which is NOT in a soluble form within said culture broth is protein of interest which is bound to solids in the culture broth such as cell solids or other solid components in the broth; or a method, wherein more than 20% of the protein of interest, at pH 7.5, which is NOT in a soluble form within said culture broth is protein of interest which is precipitated or crystallized within said culture broth.

A culture broth is generally derived from a fermentation batch.

How the actual fermentation has been carried out is relatively inessential for the recovery method of present invention.

Accordingly, the fermentation time, pH or other specific fermentation conditions may be done according to standard conditions known in the art. Preferably, the fermentation conditions are adjusted to obtain maximum yields of the protein of interest.

Further, the culture broth may be a spin down (centrifuged) fraction of a culture broth.

The term "a spin down fraction of a culture broth" denotes the fraction of a culture broth obtained after centrifugation, such as cells, insoluble substrates, and insoluble fermentation products. The insoluble fermentation products may comprise insoluble protein of interest.

Accordingly, in a further embodiment the invention relates to a method of the invention wherein the culture broth is a spin down fraction of a culture broth.

Said spin down fraction of a culture broth may be suspended or diluted in an aqueous solution such as water before the protein of interest is recovered according to the method described herein. Said suspension or dilution may be done according to the skilled person's general knowledge.

Further, any further agents or components known to the skilled person to mediate solubilization of an insoluble protein may further be added to the culture broth. Such components may be components ensuring against precipitation or crystallisation of the protein of interest.

Non-limiting examples of such components are salts, calcium, polyols, detergents, defoamers, anti-foamers, or substrate analogs/inhibitors for the protein of interest. Reference is made to WO 97/23604; EP 0574050A1 or Journal of biotechnology, 26 (1992) for further description of such suitable components.

Further, a culture broth as described herein is preferably a broth comprising a chemically defined medium. See WO 98/37179 for a further description of such a culture broth comprising a chemically defined medium.

Adjustment of pH

The pH of the culture broth may be adjusted by using any suitable strategy known to the skilled person.

Any suitable base may be used to adjust the pH. Preferred bases are sodium hydroxide, potassium hydroxide and ammonium hydroxide, in particular sodium hydroxide.

Preferably, according to step a) of the invention, the pH of the culture broth is adjusted to a pH value of from pH 9.75 to pH 13; more preferably to a pH value of from pH 10 to pH 13; even more preferably to a pH value of from pH 10.25 to pH 13; and most preferably to a pH value of from pH 10.5 to pH 13.

As stated above a culture broth may be derived from a fermentation batch.

Accordingly, the pH adjustment may be done already during the fermentation resulting in a fermentation batch having a pH value as specified in step a) of the first aspect of the invention. When and how the pH adjustment is performed is of limited importance for a method as described herein. The important thing is that the culture broth has a pH value within a range as specified herein.

The pH adjusted as described in the present invention shall preferably be maintained during the recovery process according to the specific characteristics of the protein of interest, specially the stability characteristics of the protein.

In other words, if the protein of interest is relatively unstable at high pH, it may be preferred first to adjust the pH as described herein to solubilize the protein; followed by a relatively rapid recovery of the solubilized protein according to item b) of the first aspect of the invention; and then shortly thereafter adjust the pH to a level where the protein remains relatively stable over time; or, alternatively, first adjust the pH to a high pH and then immediately after solubilization of the protein adjust the pH to a lower pH before separation.

On the contrary, if the protein of interest is relatively stable at high pH, the pH level adjusted as described under item a) of the first aspect of the invention may be maintained over a relatively longer period of time.

It is within the skilled person's general knowledge to optimize the specific time period said adjusted pH level should be maintained in relation to the specific characteristics of the protein of interest to be recovered.

Further, the general problem to be solved herein, i.e. to recover a protein of interest where a significant amount of the protein of interest is not in solution is most pronounced when the protein of interest is expressed at relatively high yields.

Consequently, a preferred embodiment of the invention is a culture broth wherein the protein of interest is expressed in an amount of at least 2 g protein (dry matter)/kg culture medium; preferably in an amount of at least 3 g protein (dry matter)/ kg culture medium; more preferably in an amount of at least 5 g protein (dry matter)/kg culture medium, and most preferably in an amount of at least 10 g protein (dry matter)/kg culture medium.

A Cell Capable of Producing the Protein of Interest

A cell capable of producing the protein of interest may in principle be any cell such as a microbial cell, a plant cell or a mammalian cell.

Preferably said cell is a microbial cell and in particular a bacterial cell or a fungal cell. The present invention is especially suited for bacterial cells.

A bacterial cell is preferably a Bacillus cell, and a fungal cell is preferably a filamentous fungal cell such as an Aspergillus or a *Fusarium filamentous* fungal cell.

Use of Flocculation Agents

Preferably, the culture solution in step a) of the present invention is further treated with one or more flocculation agent(s).

The flocculation agent(s) may be added to the culture broth and/or to a fermentation batch/broth before, during, or after the actual pH adjustment.

Flocculation agents are known in the art and are specially used to provide a protein solution (e.g. a culture broth as defined herein comprising a cell producing a protein of interest) which is particularly well fitted for centrifugation, filtration, or for membrane concentration/filtration as the flux as well as the purity of the protein is increased.

Preferably, the flocculation agent(s) is a soluble Fe and/or Al compound.

Use of such soluble Fe and/or Al compounds as flocculation agent(s) are known from WO 96/38469.

However, in the WO 96/38469 disclosure on page 7, line 13–14 it is stated that "It is important that the pH of the fermentation broth is kept between pH 4 and pH 9".

Accordingly, said WO 96/38469 disclosure describes a solution having as an essential element, pH values from 4 to 9, which are pH values outside the scope of the pH values used in a recovery method of the present invention.

Preferably, the culture broth is treated with from 0.02 moles to 1.2 moles Al/Fe compound per liter of culture solution, more preferably the culture broth is treated with from 0.04 moles to 1.0 moles Al/Fe compound per liter of culture broth.

According to the invention, any soluble Fe or Al compound, or any mixture thereof, may be used, such as $Al_2(SO_4)_3$, $NaAlO_2$, $K_2Al_2O_4$, $Al(NO_3)_3$, $AlCl_3$, Al-acetate, Al-formate, $Fe_2(SO_4)_3$, Fe(III)-formate, Fe(III)-acetate, Fe(II)-formate and Fe(II)-acetate.

The preferred compound is a polymer aluminum hydroxychloride (e.g. EKOFLOCK available from Boliden), a polymer aluminum chlorohydrate (available from Calgon corporation), or $NaAlO_2$.

Stabilizers

According to the present invention, it may in some cases be a good idea to add a stabilizer (so that the protein of interest is able to increase its ability to tolerate the high pH) or a protease inhibitor (so that the protein of interest is not degraded). Useful protease inhibitors include, without limitation, a boric acid or a boronic acid, especially 4-formyl-phenyl-boronic acid as described in WO 96/41859.

Removing the cells from the broth to obtain a solution comprising the protein of interest:

The separation according to step b) of the present invention may be performed according to any standard known methods.

Such methods may be one or more solid/liquid separatory techniques such as centrifugation, filtration, or micro filtration.

A Protein of Interest

The method of the invention can be applied for recovering any protein of interest.

Preferably, the protein of interest is an enzyme, in particular an enzyme classified as a glycosidase (EC 3.2) or an enzyme classified as a peptidase (EC 3.4); (EC-numbering according to Enzyme Nomenclature, Recommendations (1992) of the Nomenclature Committee of the International Union of Biochemistry and Molecular Biology). Especially preferred enzymes are enzymes selected from the group consisting of an amylase (in particular an α-amylase (EC 3.2.1.1)), a cellulase (EC 3.2.1.4), a lactase (EC 3.2.1.108), a xyloglucanase, a mannanase (EC 3.2.1.25), and a protease; in particular an enzyme selected from the group consisting of an amylase, a mannanase and a protease. This preferred group of enzymes very often presents problems during recovery due to precipitation and/or crystallization.

Further, protein engineered variants, made by recombinant DNA techniques, of a protein of interest (preferably an enzyme of interest) may be of particular interest.

This is due to the fact that such variants can many times give unexpected problems during recovery, such as they precipitate or crystallize.

Such protein engineered variants may e.g. be a protease variant or an amylase variant, especially a variant which have increased hydrophobicity and/or decreased solubility in culture solutions. Preferably, the protein of interest is a protein that has at least 80% residual activity after 20 minutes incubation, 5° C.; at pH 9.5; more preferably at least 80% residual activity after 20 minutes incubation, 5° C.; at pH 10.0, and most preferably at least 80% residual activity after 20 minutes incubation, 5° C.; at pH 11.

EXAMPLE 1

An α-amylase variant produced as described in WO 96/23873 was fermented.

After fermentation it could be seen in a microscope (400X) that there were enzyme crystals in the culture solution.

The α-amylase activity of the culture solution was measured to 100%.

The culture solution was centrifuged at pH 7.5.

After centrifugation the supernatant had an α-amylase activity of 20.4%.

The relation of solubilized/(solubilized+non-solubilized) is therefore (see page 4):
(Prot. conc, sup./Prot. Conc, cul)*100<80)=20.4%/ 100%*100=20.4, (which is far below the limit of 80).
Flocculation The following chemicals were added to two culture samples of 100 g each (under stirring conditions):

200% water; 1% $CaCl_2$, $2H_2O$; 0.2% $NaAlO_2$; 0.3% Superfloc C 521 and 0.3% Superfloc A 130. During the addition of the chemicals pH was kept at pH 7.5 in one sample and at pH 10.5 in the second sample—the pH was kept at 7.5/10.5 for about 10 min; temperature was room temperature (approximately 20° C.).

The two samples were then centrifuged, and the yield of α-amylase activity was determined in the supernatant fraction:

Yield trial 1 (pH 7.5):=45%
Yield trial 2 (pH 10.5):=80%

The above described tests clearly show that an alcaline treatment of the sample dramatically increases product yield.

What is claimed is:

1. A method for recovering a glycosidase or a peptidase from a culture broth comprising a culture medium and the cells which have produced the glycosidase or peptidase, wherein less than 80% of the peptidase or glycosidase in the culture medium is soluble in the culture medium and the remaining peptidase or glycosidase in the culture medium is present in the culture medium as either a precipitate or in crystalline form, comprising the sequence:

a) adjusting the pH of the culture broth, which contains both the culture medium and the cells, to a pH value between about 9.5 and about 13, and subsequently, b) removing the cells from the culture broth to obtain the culture medium which contains the glycosidase or peptidase.

2. A method as defined in claim 1, wherein said remaining peptidase not in a soluble form at pH 7.5 is bound to solids in the culture broth.

3. A method as defined in claim 1, wherein the broth is adjusted to a pH between about 9.75 and about 13.

4. A method as defined in claim 1, wherein the broth is adjusted to a pH between about 10 to 13.

5. A method as defined in claim 1, wherein, in step (i), the culture broth is treated with at least one flocculation agent before, during, or after the pH adjustment.

6. A method as defined in claim 5, wherein the flocculation agent is a soluble Fe or Al compound.

7. A method as defined in claim 6, wherein the Al compound is selected from the group consisting of aluminum hydroxychloride, a polymer aluminum chlorohydrate, and $NaAlO_2$.

8. A method as defined in claim 1, wherein the glycosidase or peptidase is a recombinantly derived variant.

9. A method as defined in claim 1, wherein the glycosidase is an amylase or a mannanase.

10. A method as defined in claim 1, wherein the peptidase is a protease.

11. A method as defined in claim 1, further comprising, prior to step (b), adjusting the pH to a lower pH.

* * * * *